(12) United States Patent
Wiedenbein

(10) Patent No.: US 7,628,272 B2
(45) Date of Patent: Dec. 8, 2009

(54) CONTAINER FOR HOLDING CLAMPS

(75) Inventor: Wolfgang Wiedenbein, Seelze (DE)

(73) Assignee: Cardiomedical GmbH, Langenhagen, DE (US)

( * ) Notice: Subject to any disclaimer, the term of this patent is extended or adjusted under 35 U.S.C. 154(b) by 248 days.

(21) Appl. No.: 11/813,777

(22) PCT Filed: Jun. 20, 2006

(86) PCT No.: PCT/DE2006/001039

§ 371 (c)(1),
(2), (4) Date: Jul. 12, 2007

(87) PCT Pub. No.: WO2007/033628

PCT Pub. Date: Mar. 29, 2007

(65) Prior Publication Data

US 2008/0164169 A1    Jul. 10, 2008

(30) Foreign Application Priority Data

Sep. 21, 2005    (DE) ................ 10 2005 045 006

(51) Int. Cl.
*B65D 85/24* (2006.01)
(52) U.S. Cl. ...................... 206/339; 206/341
(58) Field of Classification Search ............... 206/63.3, 206/338–341; 606/151, 157–158
See application file for complete search history.

(56) References Cited

U.S. PATENT DOCUMENTS

| | | | |
|---|---|---|---|
| 3,323,216 A | 6/1967 | Ublacker | |
| 3,363,628 A | 1/1968 | Wood | |
| 4,076,120 A | 2/1978 | Carroll | |
| 4,936,447 A | 6/1990 | Peiffer | |
| 4,972,949 A * | 11/1990 | Peiffer | ........................ 206/339 |
| 5,046,611 A | 9/1991 | Oh | |
| 5,279,416 A * | 1/1994 | Malec et al. | ................. 206/339 |
| 6,158,583 A * | 12/2000 | Forster | ........................ 206/339 |
| 6,273,253 B1 | 8/2001 | Forster | |
| 6,460,700 B2 * | 10/2002 | Weisshaupt | ................. 206/339 |

FOREIGN PATENT DOCUMENTS

| | | |
|---|---|---|
| DE | 19903752 C1 | 3/2000 |
| FR | 2091762 | 1/1972 |
| WO | WO 98/05260 | 2/1998 |

OTHER PUBLICATIONS

PCT Translation of International Preliminary Report on Patentability and Written Opinion of the ISA.
PCT International Search Report for PCT/DE2006/001039.

* cited by examiner

*Primary Examiner*—Bryon P Gehman
(74) *Attorney, Agent, or Firm*—Robert C. Haldiman; Husch Blackwell Sanders LLP

(57) ABSTRACT

Hemostatic clamps are used to tie or clamp blood vessels during surgical procedures. Special containers are used to store and advantageously provide hemostatic clamps. These containers completely and clearly hold clamps in each phase without tilting, and enable reliable removal by a surgeon using a surgical instrument. This is achieved with the container according to the invention, which avoids friction between the clamp and the surgical instrument.

20 Claims, 4 Drawing Sheets

CONTAINER FOR HOLDING CLAMPS

CROSS-REFERENCE TO RELATED APPLICATIONS

This application claims priority to international application PCT/DE2006/001039, filed Jun. 20, 2006 and German application DE 10 2005 045 006 filed on Sep. 21, 2005.

BACKGROUND OF THE INVENTION

1. Field of the Invention

This invention generally relates to the area of medicine in the surgical field. Containers are used in surgery for application tools for applying objects. Some containers are especially suitable for holding special objects, in particular hemostatic clamps. Hemostatic clamps are also referred to as ligature clamps. Ligature clamps are used to tie or clamp blood vessels during surgical procedures, and kept in containers. These containers usually consist of holders, cassettes or magazines. The invention relates to such a magazine.

2. Related Art

Ligature clamps have been used in surgery for many years. They serve two basic functions, specifically tying vessels, nerves or fluid-carrying vessels of the human body, or marking a special surgical site, typically the periphery of a tumor, for example, which can later be seen in an X-ray. The ligature clamps (hereinafter referred to as clamps) are available in three basic sizes-small, medium and large, as well as in two special sizes combination small/medium and impervious to X-rays. Clamps used early on were V-shaped. However, the disadvantage to clamps shaped like this is that they pressed the vessel away from the clamp or cut into the vessel instead of tying it off. This problem was resolved through the use of pre-shaped, horseshoe-shaped clamps that were described in U.S. Pat. Nos. 3,323,216 and 3,363,628 and are currently in general use. The horseshoe-shaped clamp consists of two essentially parallel legs, which initially fix the vessel between the ends when closed, thereby holding it between the actual ligature between the ends.

In a typical magazine for holding and providing clamps in the prior art, a plurality of side-by-side clamps, e.g., ten, are pressed onto a rigid middle beam or pillow block. The outer shape of the pillow block corresponds to the inner shape of the horseshoe-shaped clamps. However, the clamps are somewhat smaller than the pillow block, so that the contact pressure between the parallel legs of the clamp and the pillow blocks holds the clamps during transport and prevents the clamps from falling out of the magazine if the magazine is turned or dropped. But this contact pressure is associated with several disadvantages. First of all, the contact pressure makes it hard to grip the clamp via the clamping jaws or branches of an application tool, in particular the special forceps. Secondly, it makes removal a very unsafe process, even though the application tool has two branches that can move relative to each other, the free ends of which each carry longitudinal grooves on the facing sides that run parallel to the branches and are open relative to the opposing branch. Application tools with a narrow clamping jaw width make it more difficult to grip the clamp, especially since the clamp already tightly abuts the pillow block, and therefore cannot be compressed. This significantly increases the friction between the application tool and the clamp, and metal might be shaved off the clamp. If the clamping jaws of the application tool are too wide, the clamp is sometimes not reliably gripped by the clamping jaws after removed from the magazine. As a result, the clamp might slip from the operating position inside the application tool or fall out of the application tool. Another disadvantage is that the contact tension makes it difficult to remove the clamp from the holding device of the magazine. The tight abutment between the clamp and pillow block generates significant friction between the pillow block and clamp, and the relatively small magazine must be held to enable removal. The required handling of the clamp and magazine is associated with additional disadvantages.

Further developments in prior art are intended to eliminate the above disadvantages. For example, U.S. Pat. No. 4,936,447 discloses a cassette for holding ligature clamps, in which the downwardly open end of the ligature clamps is plugged into a free compartment via a nose saddle, and both sides of its outer contour are held by a respective elastic holding device provided with a notch at the end. The holding device is designed with a special insert, which must additionally be connected with the basic body of the cassette. The notches on the holding device must reliably grip the ligature clamps, but easily release them again during removal by means of an application tool provided for this purpose. In the known cassette, the holding devices must be manufactured to exacting tolerances with respect to dimensions and resilience. They are also only suitable for mounting a single type of ligature clamp. Even if this magazine embodiment makes it possible to eliminate the aforementioned friction disadvantages, there remains the problem that the application tool and retaining straps disrupt each other, since these abut the arms of the clamps, which happen to form the areas into which the forceps reaches. This is the cause of disruptions. Another serious disadvantage to this cassette is that it has no guide for the application tool for removing the ligature clamps. Therefore, disadvantages are associated with handling when gripping the ligature clamps, i.e., the ligature clamp is not optimally situated in the application tool, so that mistakes can be encountered when tying off the vessels.

In the magazine described in WO 98/05260 A1 and the publications cited therein, each clamp sits astride a fixed element (reverse position with "U" turned upside down) with a complementary shape, which is seamed by a pair of massive transverse walls used to hold the clamps. The clamps incorporated in such a magazine are in part very small, e.g., the dimensions measure on the order of 1.5 mm, making it extremely difficult to handle the clamps. In the known magazines, the clamps are held in such a way that a forceps-like application tool can grasp the clamps when inserted into a magazine, and then pull them out of the magazine. The disadvantage to known magazines here is that the clamps are fixed laterally by elastically resilient clamping elements, which only abut the middle area of the web, and are lifted during the insertion of an application tool. Therefore, the clamps might become tilted or even jammed in the magazine while inserting the application tool, then making it impossible to introduce the clamp into the application tool in the manner envisaged.

Another problem is encountered in holding devices in clamp magazines according to prior art. In order to ensure that the application tool encompasses the clamps, the clamping jaws of the application tool must be stronger than the clamps. To allow the application tool to reach into the clamp compartment, this compartment must therefore be wider than the clamp. As a result of the wider clamp, the clamp can be varyingly positioned in the compartment as the application tool enters, and not be centered, so that the clamp is not gripped precisely by the middle of the application tool. A clamp not correctly gripped by the clamping jaws of the application tool can cause the clamp to close unevenly. The principle for removing the clamps from a magazine is identical for all known clamp sizes. The magazines for the varying clamp sizes are color-labeled for differentiation purposes. For example, the magazine accompanying the small clamp size is yellow, while it is blue for medium and orange for large.

There is a need therefore, for an inexpensive container with a simple functional geometry to hold hemostatic clamps, with elevated demands on safe storage and removal, and hence on tying off vessels, exhibiting a structural shape suitable for reliably removing clamps via a surgical instrument.

SUMMARY OF THE INVENTION

In order to create a container exhibiting these features of the invention for holding hemostatic clamps, in particular ligature clamps for surgery, the invention proposes that a container be designed in such a way that the clamps in the container are completely and clearly held without tilting, in particular when introducing a surgical instrument (hereinafter referred to as application tool) into the container. The invention is a container that consists of two components for holding a plurality of storable and retrievable objects, in particular ligature clamps, of which each is formed in a specific mold and can be gripped by an application tool. The two components consist of a lower and upper part. The lower part is fitted with a plurality of clamp compartments, of which each contains at least one lateral wall for bordering the clamping elements and a pillow block for loosely storing the clamp. The upper part is provided with a plurality of clamping elements for holding the clamp in each of the clamp compartments, wherein a clamping element consists of two movable retaining means, which envelope the pillow block in each of the clamp compartments, and of which each retaining means has a contact section that holds the respective clamp on the pillow block.

The device according to the invention is used in practice as described below. This description is not to be construed as a limitation, but rather serves to describe the general principle underlying the invention.

In general, this invention has a container consisting of a lower and upper part, wherein the lower part represents the retaining device. The basic part is provided with a plurality of clamp compartments, advantageously with six to ten compartments, each of which can hold a prefabricated ligature clamp. Therefore, each compartment has a pillow block that is dimensioned in such a way as to roughly correspond to the interior dimensions of a ligature clamp, and holds the clamp loosely in the clamp compartment. In order to prevent the clamp from being held by friction, the pillow block has a channel according to the invention. The channel is arranged in the transverse direction to the pillow block and formed on the outer contour of the pillow block, or on the middle line of the pillow block, wherein the middle line of the pillow block is simultaneously the middle line of the clamp compartment. Another advantage to the channel is that the clamp can be centered when fitting the basic part onto the pillow block. This is also necessary because the clamp compartment with pillow block contained therein is larger than the ligature clamp. The size of the clamp compartment is determined by the size of the application tool to be used, which has to be larger in order to grasp the ligature clamp.

Therefore, the application tool determines the size of the clamp compartment, and the channel determines the location of the clamp on the pillow block, and hence in the clamp compartment. If the basic part of the container is fitted with one clamp per clamp compartment, which may also occur automatically as a result of the simple and advantageous construction of the basic part, e.g., with a automatic pick and place machine known from SMD technology, the basic part is fabricated with the retaining device.

During fabrication, the webs and separating walls arranged on the basic part according to the invention pass through openings situated in the retaining device, wherein the retaining device can be secured to the basic part in various sways, e.g., via bonding or latching on connecting pins projecting at the corners of the upper side of the basic part, wherein the retaining device has the correspondingly necessary holes at the corners. As an alternative, the pins may also be arranged on the lower side of the retaining device, and the holes in the basic part. Other fastening modes or connections between the basic part and retaining device are within the scope of the invention.

As evident from one embodiment of the container, the clamp centered in the chamber of the pillow block of the basic part is held by a clamping element, wherein the clamping element is formed out of two retaining means per clamp compartment, which envelop the pillow block in the fabricated state. To this end, the retaining means is U-shaped. The clamping element is hence formed out of a pair of retaining means, and holds the clamp between the latter two. As a result, the clamp is clamped from both sides. Clamping takes place via the retaining means in the contact area that are fitted with a latching nose. The latching nose is located at the vertex of the retaining means, and points in the direction of the clamp. In order for the clamp attached in the channel of the pillow block to yield a detachable clamping, the U-shaped retaining means are flexibly arranged on the retaining device. The flexibility stems from the fact that the legs of the retaining means are relatively thin, and secured to the retaining device only at their ends, yielding a certain mobility of the retaining means. Because the U-shaped strap of the retaining means is inclined, the material causes a specific tension (spring force) to be exerted on the clamp inserted in the channel.

To advantageously remove a clamp from a clamp compartment of a container, the basic part according to the invention is fitted with webs arranged on both longitudinal sides of the basic part on the one hand, and the pillow blocks located in the clamp compartment are provided with a pedestal on the other. The webs are used by the application tool to guide the clamping jaws, while the pedestals are used by the front surfaces of the application tool as a solid stop.

A clamp is removed with an application tool by inserting the application tool from above between the webs of a clamp compartment on the one hand, and between the two retaining means of a clamping element on the other. The inclined guiding surface on the webs according to the invention leads the application tool against the U-shaped straps of the retaining means, during which the retaining means are forced apart, and the application tool is fixed against the clamp. The application tool reaches its end position once the front surfaces of the two clamping jaws hit the stop of the pedestal, i.e., the insertion depth of the application tool is limited by the stop formed by the pedestal on the pillow block. Once the application tool has been inserted, the clamping jaws of the application tool are optimally situated relative to the clamp. The two legs of the clamps are defined in this position of the application tool in the channels of the two clamping jaws. The leg ends of the clamp are now flush with the ends of the clamping jaws of the application tool. The webs of the U-shaped retaining means according to the invention and the pedestal stop on the pillow bearing ensures a frictionless removal of the clamp from the pillow block, and no friction comes about when introducing the application tool between the chamber and clamping jaws either.

An exemplary embodiment of the invention is depicted in purely a schematic form in the drawings, and will be described in greater detail below.

DETAILED DESCRIPTION

Figure 1:
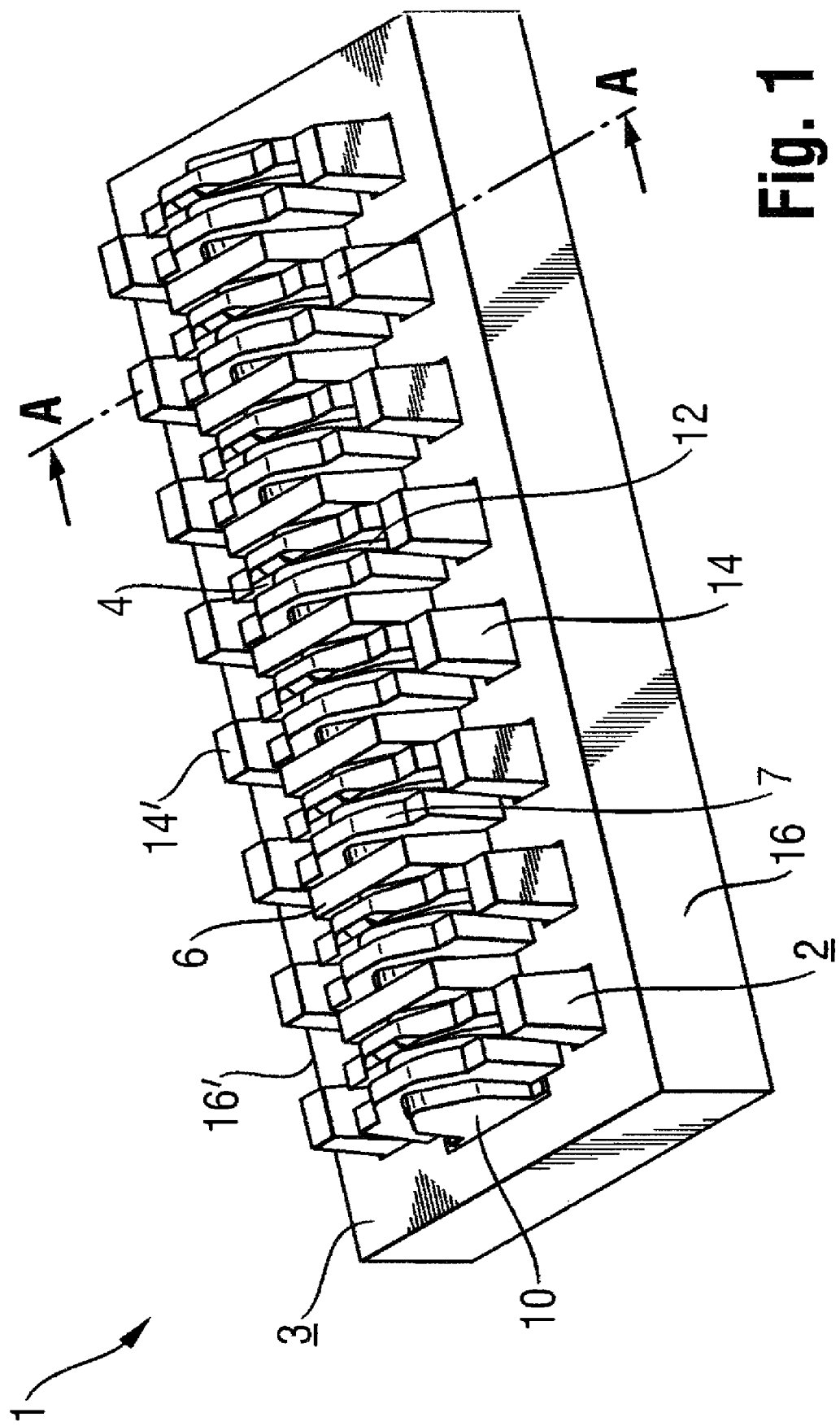
FIG. 1 is a perspective view of a container for holding a plurality of hemostatic clamps.

FIG. 1 shows a perspective view of a container 1 for ligament clamps 12, consisting of a lower base 2 and upper 3 part, wherein the lower base part 2 represents the basic part and the upper part 3 represents the retaining device. The basic part 2 is fitted with a plurality of clamp compartments 4 (see also FIG. 2), of which each has at least one lateral wall 5 for limiting the clamping element 7 and a pillow block 10 for loosely storing the clamps 12, wherein the pillow block 10 matches the contour 11 of the clamp 12. In addition, the basic part 2 is provided with a plurality of webs 14, wherein each clamp compartment 4 accommodates two webs 14, 14', and the webs 14, 14' are used to guide the application tool 15 (see FIG. 4) for reliably removing the clamp 12. The webs 14, 14' are arranged on the longitudinal sides 16, 16' of the basic part 2 at a specific distance X in the longitudinal direction 17 relative to each other, and at a specific distance Y in the transverse direction 18 of the transverse side 19 relative to the pillow block 10. This arrangement of the webs 14, 14' in a longitudinal 17 and transverse 18 direction yields two webs 14, 14' per clamp compartment 4, which are centrally arranged relative to the clamp compartment 4, and located on the middle line Z of the transverse direction 18 relative to the pillow block 10. The middle line Z in the area of the pillow block 10 incorporates a channel 13 in its outer contour 11. The channel 13 is used to center the clamp 12 on the pillow block 10, and is adjusted to the inner contour 9 of the clamp 12 (not shown). The clamp 12 is loosely accommodated in the channel 13. The height of the pillow block 10 and height of the lateral wall 5 may correspond to the height of the webs 14, 14'. The basic part 2 may be one-piece, and can be made out of various materials, preferably out of a plastic that serves medical purposes and resists sterilization. The sectional view A-A through the container 1 is evident from FIG. 4.

Figure 2:
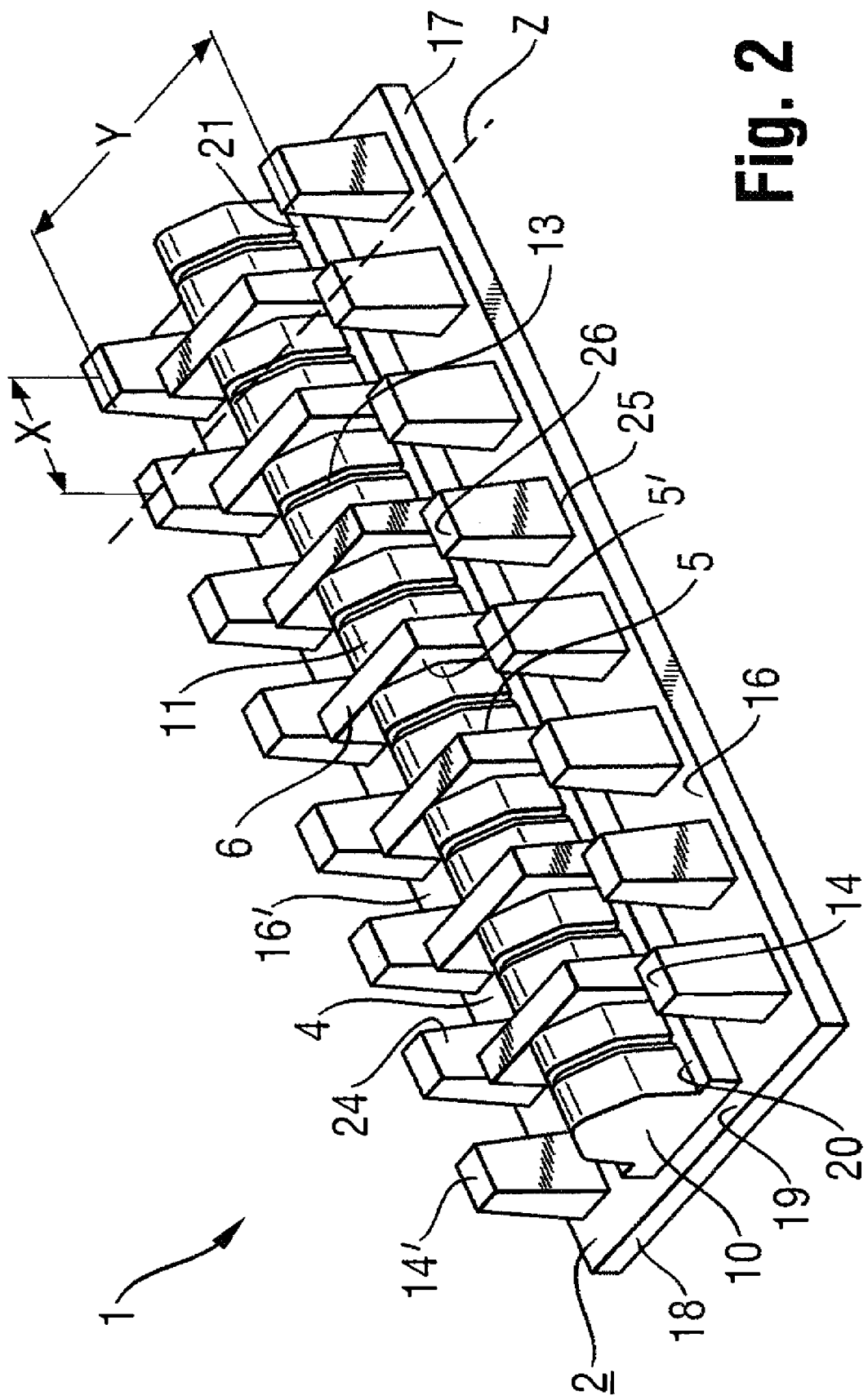
FIG. 2 is a perspective view of the basic part.

As the basic part 2 on FIG. 2 shows, the pillow block 10 has another function according to the invention. The function involves equipping the pillow block 10 with a pedestal 20. The pedestal 20 runs in the longitudinal direction 17 of the basic part 2 on either side of the pillow block 10. The upper side 21 of the pedestal 20 serves as a stop for the front faces 23 of the clamping jaws 22 of the application tool 15 (see FIG. 4). In addition, the surface 24 of the webs 14, 14' is inclined on the side facing the pillow block 10. Therefore, the base surface 25 of the webs 14, 14' narrows toward the top end. As a result, the distance of the webs 14, 14' in a clamp compartment 4 viewed in the transverse direction 18 is smaller in the base area than in the top area due to the inclined surface 24. The shortened distance between the two webs 14, 14' of a clamp compartment 4 automatically presses the application tool 15 against the retainers 8 in a first step in order to open the latter, and guides it against the clamp 12 in a second step, which is situated between the two retainers 8 to remove them.

Figure 3:
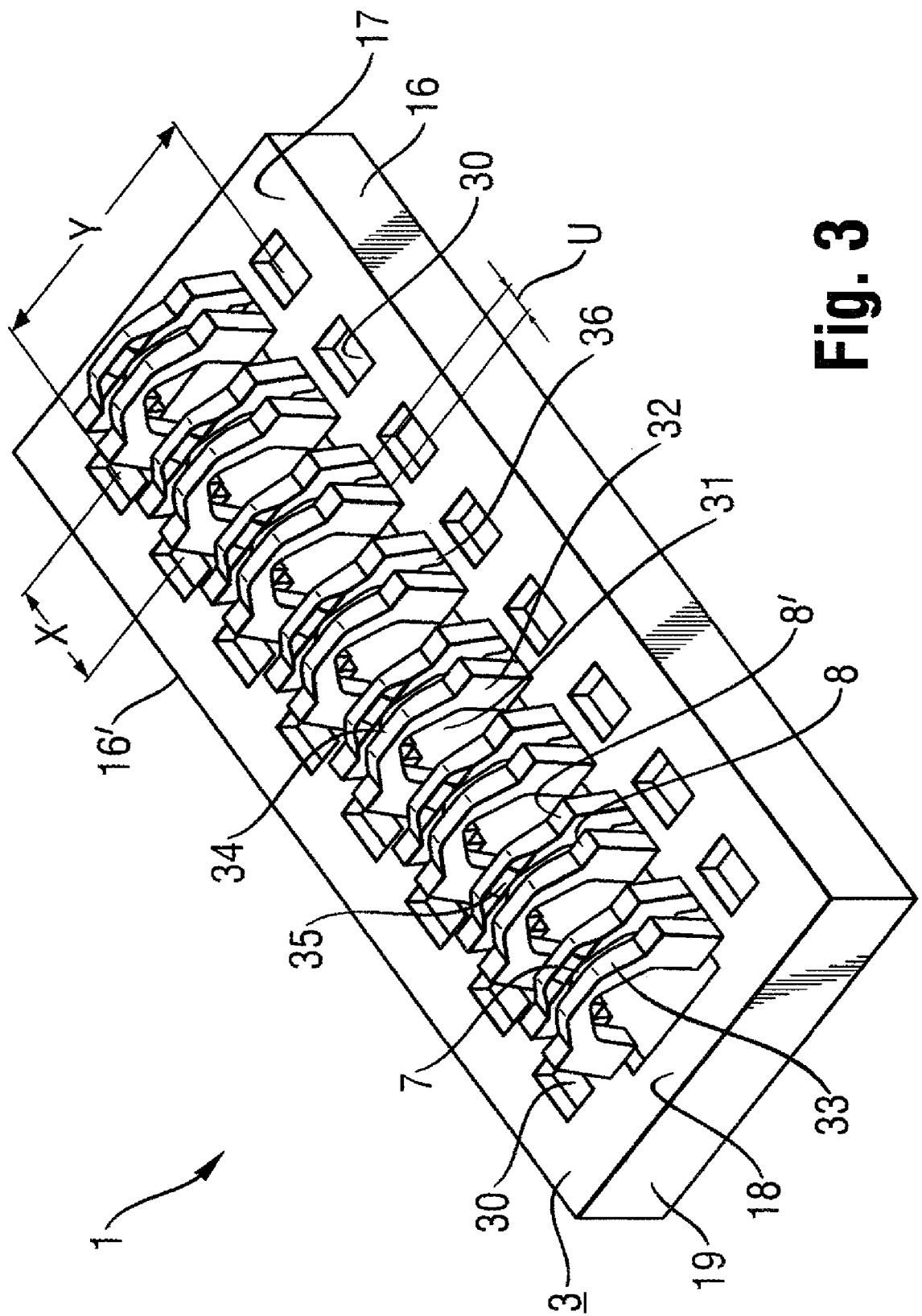
FIG. 3 is a perspective view of the retaining device.

As evident from FIG. 3, the retaining device or base cover 3 has openings 30 through which the webs 14, 14' of the basic part 2 can extend, and openings 31 that accommodate separating walls 6. The openings are situated at both longitudinal sides of the retaining device 3 at a certain distance X in the longitudinal direction relative to each other, and at a certain distance Y in the transverse direction similarly to the webs 14, 14' in the basic part 2, wherein the shape of the openings 30 for accommodating the webs 14, 14' matches their shape. Other openings 31 in the retaining device 3 are used to accommodate the separating walls 6 of the basic part 2 during fabrication. The openings 31 are located between the adjacent clamping elements 7, and a separating wall 6 has two lateral walls 5, 5', which serve as a lateral stop for the retainers 8, 8' (see FIG. 2). In addition, the retaining device 3 is fitted with a plurality of clamping elements 7, wherein one clamping element 7 is allocated to each clamp compartment 4. A clamping element 7 here consists of two paired retainers 8, 8', with there being one pair per clamp compartment 4. The retaining means 8, 8' are U-shaped, wherein the legs 32 of the U-shaped strap 33 project from the retaining device 3. The vertex area 34 or contact area of the U-shaped strap 33 has a latching nose 35, which assumes the function of holding the clamp 12 on the pillow block 10. The retainers 8, 8' are inclined, and meet at the vertex 34. The distance "U" of the paired retainers 8, 8' in the base area 36 of the straps 23 is selected in such a way that the clamping jaws 22 of the application tool 15 can be easily introduced between them. The clamping jaws 22 reach between the retainers 8, 8' in a horizontal direction according to the invention, such that no forces act on the container in a tangential direction. The U-shaped strap 33 is biased towards a retaining position.

In the depicted embodiment the retaining position holds latch 35 over a top surface of the clamp. As the clamping jaws 22 are introduced further, the retaining means 8, 8' are bent apart in the vertex area 34, causing the latching noses 35 to release the clamp 12. The maximum path that a retaining element 8, 8' can traverse from the closed setting to the open setting is limited by the lateral walls 5, 5' of the separating wall 6. This precludes any excess bending of the retaining means 8, 8. If the retainers 8, 8' abut the lateral walls 5, 5', the clamp 12 is free, and can be removed from the pillow block 10 by the application tool 15 without friction.

Figure 4:
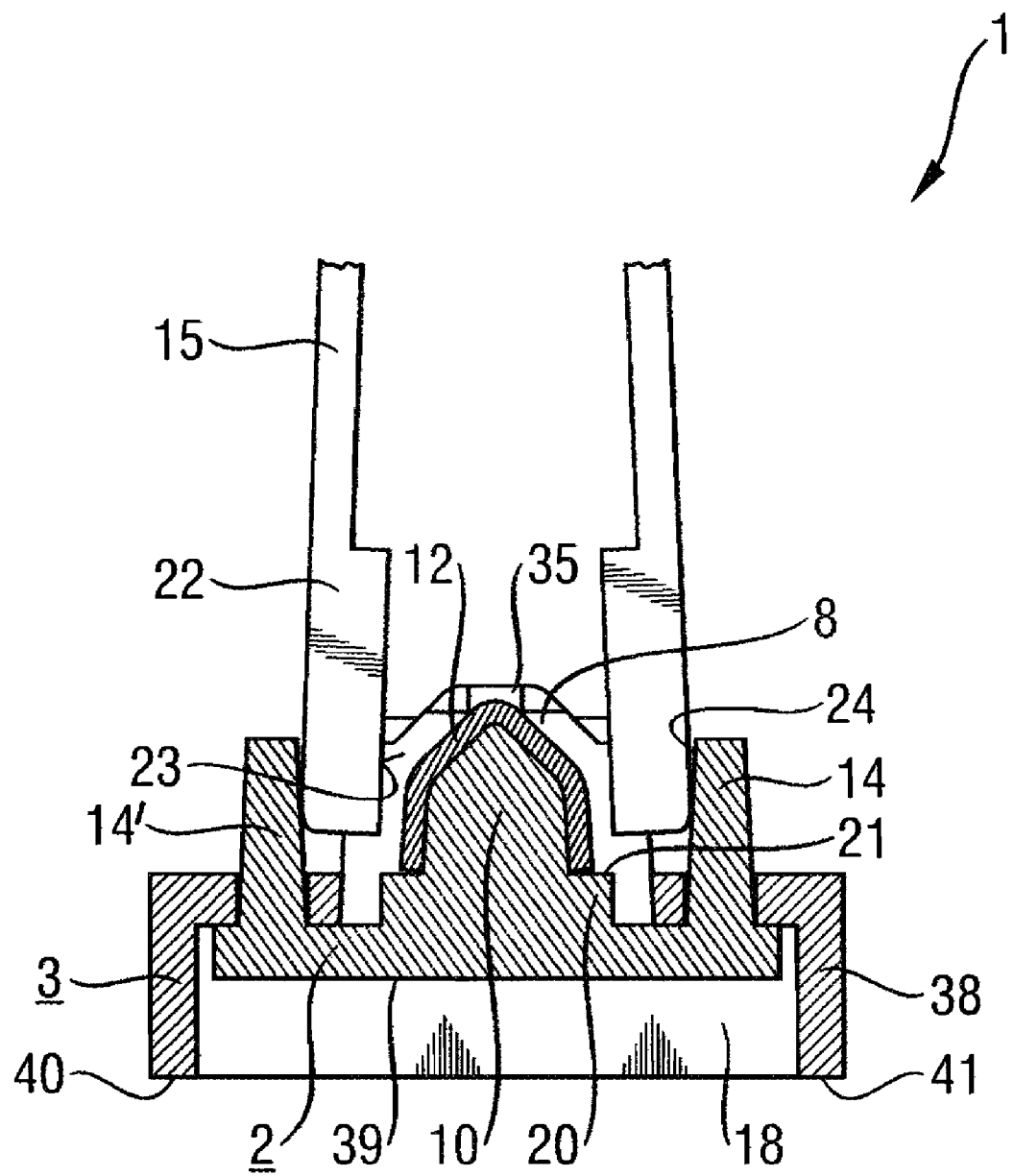
FIG. 4 is a sectional view A-A through the container on FIG. 1

FIG. 4 shows a sectional view A-A of the container 1 fitted with a clamp 12 according to FIG. 1, consisting of a basic part 2 and the retaining device 3, wherein the upper part 3 is advantageously provided with a bordering 38. The bordering 38 can improve incorporation of the basic part 2 on the one hand, and ease handling by the user on the other. A fastening means 41 (not shown) can be provided on the lower side 39 of the basic part 2 or on the lower side 40 of the bordering 38. The fastening means 41 consists of a carrier provided on either side with a fixation, which may be double-sided adhesive tape, or alternatively a rigid foam product. As also evident form the sectional view A-A, the clamp compartment 4 is limited in the transverse direction 18 by the webs 14, 14' and in the longitudinal direction 17 by a lateral wall 5. Visible in the middle of the clamp compartment 4 is the pillow block 10 on the pedestal 20, wherein the pillow block 10 carries a clamp 12. The clamp 12 is clamped by the latching nose 35 of a retaining means 8. Schematically depicted on the inclined surface 24 of the webs 14, 14' are clamping jaws 22 of an application tool 15 that have not yet reached the end position for removing the clamp 12. At the end position, the front faces 23 of the clamping jaws 22 would be on the top side 21 of the pedestal 20, and the clamp 12 would be accommodated by the channels in the clamping jaws 22, so that the loose clamp can be removed without friction.

REFERENCE LIST

1 Container
2 Lower part (base)
3 Upper part (device)
4 Clamp compartment
5 Lateral wall
5' Lateral wall
6 Separating wall
7 Clamping element
8 Retaining means
8' Retaining means
9 Inner contour
'10 Pillow block
11 Contour
12 Clamp
13 Channel
14 Web
14' Web
15 Application tool
16 Longitudinal side
16' Longitudinal side
17 Longitudinal direction
18 Transverse direction
19 Transverse side
20 Pedestal
21 Upper side
22 Clamping jaw
23 Front face
24 Inclined surface'
25 Base surface
26 Top surface
27 Free
28 Free
29 Free
30 openings (webs)
31 Openings (lateral wall)
32 Leg
33 Strap
34 Vertex
35 Latching nose
36 Base area
37 Free
38 Bordering
39 Lower side (for 2)
40 Lower side (for 3)
41 Fastening means

What is claimed is:

1. A container for accommodating a plurality of storable and retrievable objects, of which each is formed in a specific mold and can be gripped by an application tool, wherein the container comprises:
    a lower part with a plurality of clamp compartments, each containing at least one lateral wall bordering a clamping element and a pillow block for loosely storing a retrievable object, wherein a contour of the pillow block matches a contour of the retrievable object;
    an upper part with a plurality of clamping elements for holding the retrievable object in each of the clamp compartments, wherein the clamping elements consist of two movable retainers, said retainers enveloping the pillow block in each of the clamp compartments, and each retainer having a contact section that holds the respective retrievable object, the lower part having a plurality of webs, wherein each clamp compartment accommodates two webs, and the said two webs are disposed to guide the application tool for removing the retrievable object.

2. The container according to claim 1, characterized in that the webs of the lower part are at a preconfigured distance in a longitudinal direction and at a preconfigured distance in a transverse direction relative to the pillow block.

3. The container according to claim 1, characterized in that the two webs allocated per clamp compartment are centrally located relative to the clamp compartment.

4. The container according to claim 1, characterized in that each web is arranged in a transverse direction relative to the pillow block on its middle line.

5. The container according to claim 1, characterized in that each web has an inclined surface, and the inclined surface corresponds to the side facing the pillow block.

6. The container according to claim 1, characterized in that a middle line on an outer contour of the pillow block has a channel for centering the retrievable object.

7. The container according to claim 1, characterized in that the pillow block is provided with a pedestal.

8. The container according to claim 1, characterized in that a height of each web corresponds to a height of the separating wall and the height of the pillow block.

9. The container according to claim 1, characterized in that the lower part is one-piece.

10. The container of claim 1, wherein the retrievable objects are ligature clamps.

11. The container of claim 1 further comprising each of said webs having an inwardly facing wall, to opposing ones of said inwardly facing walls defining therebetween a channel dimensioned to receive an application tool and guide the application tool's engagement with one of the retrievable objects retained within said channel, the engagement thereby enabling removal of the retrievable object with the application tool.

12. The container of claim 11, wherein further comprising said channel being a constricting channel.

13. The container of claim 1 further comprising a retainer, said retainer being disposed between said clamping elements and said webs such that said retainer retains one of the retrievable objects.

14. A container for accommodating a plurality of storable and retrievable objects, of which each is formed in a specific mold and an be gripped by an application tool, wherein the container exhibits the following:
    a lower part with a plurality of clamp compartments each containing at least one lateral wall bordering a clamping element and a pillow block for loosely storing a retrievable object, wherein a contour of the pillow block matches a contour of the retrievable object;
    an upper part with a plurality of clamping elements for holding the retrievable object in each of the clamp compartments, wherein said clamping elements consist of two movable retainers, said retainers enveloping the pillow block in each of the clamp compartments, and of which each retainer has a contact section that holds the respective retrievable object;
    the upper part has openings, wherein a web of the lower part extends through each of the openings, a separating wall of the lower part is of the lower part are accommodated in each of the openings.

15. The container according to claim 14, characterized in that the openings on the longitudinal sides are at a preconfigured distance in a longitudinal direction relative to each other, and at a preconfigured distance in a transverse direction, similarly to webs in the lower part.

16. The container according to claim 14, characterized in that the openings for accommodating the separating walls are arranged between the clamping elements.

17. The container according to claim 14, characterized in that the retainers enveloping the pillow block are U-shaped.

18. The container according to claim 14, characterized in that the retainers are movable.

19. The container according to claim 14, characterized in that the upper part is one-piece.

20. The container of claim 14, wherein the retrievable objects are ligature clamps.

* * * * *